US007963955B2

(12) United States Patent
Freund et al.

(10) Patent No.: US 7,963,955 B2
(45) **Date of Patent: *Jun. 21, 2011**

(54) CONTAINER FOR A MEDICINAL LIQUID

(75) Inventors: Bernhard Freund, Gau-Algesheim (DE); Dieter Hochrainer, Bengen am Rhein (DE); Heinrich Kladders, Muelheim (DE); Bernd Zierenberg, Bingen am Rhein (DE); Joachim Eicher, Dortmund (DE); Johannes Geser, Dortmund (DE); Martin Essing, Dortmund (DE); Holger Reinecke, Dortmund (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1165 days.

This patent is subject to a terminal disclaimer.

(21) Appl. No.: 10/754,499

(22) Filed: Jan. 12, 2004

(65) Prior Publication Data

US 2004/0143235 A1 Jul. 22, 2004

Related U.S. Application Data

(62) Division of application No. 09/258,357, filed on Feb. 26, 1999, now Pat. No. 6,685,691.

(60) Provisional application No. 60/093,772, filed on Jul. 23, 1998.

(51) Int. Cl.
*A61B 19/00* (2006.01)

(52) U.S. Cl. ............ 604/408; 600/158; 53/390; 53/570; 222/1; 222/82; 222/105; 222/107; 222/399; 222/400.7

(58) Field of Classification Search .................. 604/408; 600/158; 53/390, 570; 222/1, 82, 105, 107, 222/399, 400.7, 541

See application file for complete search history.

(56) References Cited

U.S. PATENT DOCUMENTS 2,629,421 A 2/1953 Ayres (Continued)

FOREIGN PATENT DOCUMENTS

AU A 45520/85 1/1986

(Continued)

OTHER PUBLICATIONS

International Search Report for counterpart International Application No. PCT/EP1999/01262, European Patent Office, mailed Jul. 8, 1999, 6 pgs.

(Continued)

*Primary Examiner* — Tatyana Zalukaeva
*Assistant Examiner* — Ilya Y Treyger
(74) *Attorney, Agent, or Firm* — Michael P. Morris; Mary-Ellen M. Devlin

(57) ABSTRACT

Foil bags are used as a primary packaging for liquids, the bags permitting the liquid to be taken therefrom without the application of a considerable amount of force. A container is provided for a medicinal liquid, the container being gas-tight and liquid-tight so that it is storable over many months. The container includes a collapsible foil bag on which a flange, which is stable in respect of shape, is disposed. The flange is designed for fitting onto a discharge connection member. The container can be disposed in a casing which is stable in respect of shape. The medicinal liquid does not come into contact with air and is protected from the effect of light. The medicinal liquid may be dispensed from the foil bag in many partial quantities over a prolonged period of time, with a respective partial amount thereof being converted into an aerosol by means of an atomizer.

31 Claims, 8 Drawing Sheets

U.S. PATENT DOCUMENTS

| | | | | | |
|---|---|---|---|---|---|
| 2,952,299 | A | * | 9/1960 | Finke | 156/510 |
| 3,255,972 | A | | 6/1966 | Hultgren et al. | |
| 3,646,723 | A | * | 3/1972 | Meroney | 53/390 |
| 3,656,660 | A | | 4/1972 | Mueller | |
| 3,673,765 | A | * | 7/1972 | Dohmeier et al. | 53/570 |
| 3,878,977 | A | | 4/1975 | Carlisle | |
| 4,045,860 | A | | 9/1977 | Winckler | |
| 4,093,124 | A | | 6/1978 | Morane et al. | |
| 4,116,336 | A | | 9/1978 | Sorensen et al. | |
| 4,162,030 | A | | 7/1979 | Capra et al. | |
| 4,264,018 | A | | 4/1981 | Warren | |
| 4,322,020 | A | | 3/1982 | Stone | |
| 4,440,316 | A | | 4/1984 | Christine | |
| 4,457,454 | A | | 7/1984 | Meshberg | |
| 4,457,455 | A | | 7/1984 | Meshberg | |
| 4,469,250 | A | | 9/1984 | Evezich | |
| 4,479,989 | A | | 10/1984 | Mahal | |
| 4,519,513 | A | * | 5/1985 | Weiler et al. | 215/48 |
| 4,526,823 | A | | 7/1985 | Farrell et al. | |
| 4,559,052 | A | | 12/1985 | Babson | |
| 4,592,475 | A | | 6/1986 | Hannon et al. | |
| 4,637,934 | A | | 1/1987 | White | |
| 4,732,299 | A | | 3/1988 | Hoyt | |
| 4,760,937 | A | | 8/1988 | Evezich | |
| 4,817,830 | A | | 4/1989 | Yavorsky | |
| 4,847,462 | A | * | 7/1989 | Soodak et al. | 219/121.63 |
| 4,976,707 | A | * | 12/1990 | Bodicky et al. | 604/408 |
| 5,004,123 | A | | 4/1991 | Stoody | |
| 5,012,956 | A | | 5/1991 | Stoody | |
| 5,031,384 | A | | 7/1991 | Rebeyrolle et al. | |
| 5,038,951 | A | | 8/1991 | Rizzardi | |
| 5,102,010 | A | | 4/1992 | Osgar et al. | |
| 5,105,995 | A | | 4/1992 | Martin | |
| 5,129,894 | A | | 7/1992 | Sommermeyer et al. | |
| 5,137,175 | A | | 8/1992 | Kowalski et al. | |
| 5,158,810 | A | | 10/1992 | Oishi et al. | |
| 5,176,178 | A | | 1/1993 | Schurter et al. | |
| 5,176,654 | A | * | 1/1993 | Schreiber | 604/181 |
| 5,213,227 | A | | 5/1993 | Koyama et al. | |
| 5,242,085 | A | | 9/1993 | Richter et al. | |
| 5,275,311 | A | | 1/1994 | Piarrat | |
| 5,289,818 | A | | 3/1994 | Citterio et al. | |
| 5,292,033 | A | | 3/1994 | Gueret | |
| 5,297,537 | A | * | 3/1994 | Savitt et al. | 600/158 |
| 5,316,135 | A | | 5/1994 | Kneer et al. | |
| 5,316,221 | A | | 5/1994 | Glover et al. | |
| 5,332,121 | A | | 7/1994 | Schmidt et al. | |
| 5,337,740 | A | | 8/1994 | Armstrong et al. | |
| 5,355,872 | A | | 10/1994 | Riggs et al. | |
| 5,370,272 | A | | 12/1994 | Gueret | |
| 5,385,251 | A | | 1/1995 | Dunn | |
| 5,395,365 | A | | 3/1995 | Weiler et al. | |
| 5,421,485 | A | | 6/1995 | Furuta et al. | |
| 5,480,067 | A | | 1/1996 | Sedlmeier | |
| 5,497,909 | A | | 3/1996 | Wirsig et al. | |
| 5,497,944 | A | | 3/1996 | Weston et al. | |
| 5,507,409 | A | | 4/1996 | Paradine | |
| 5,509,578 | A | | 4/1996 | Livingstone | |
| 5,514,123 | A | | 5/1996 | Adolf et al. | |
| 5,520,972 | A | | 5/1996 | Ezaki et al. | |
| 5,520,975 | A | | 5/1996 | Inoue et al. | |
| 5,562,219 | A | | 10/1996 | de Pous et al. | |
| 5,579,760 | A | | 12/1996 | Kohler | |
| 5,642,838 | A | | 7/1997 | Stoody | |
| 5,730,326 | A | | 3/1998 | Kaeser | |
| 5,730,328 | A | | 3/1998 | Maeder et al. | |
| 5,752,629 | A | | 5/1998 | Hardy | |
| 5,772,080 | A | | 6/1998 | de Pous et al. | |
| 5,813,570 | A | | 9/1998 | Fuchs et al. | |
| 5,833,088 | A | | 11/1998 | Kladders et al. | |
| 5,873,491 | A | | 2/1999 | Garcia et al. | |
| 5,875,936 | A | | 3/1999 | Turbett et al. | |
| 5,878,915 | A | | 3/1999 | Gordon et al. | |
| 5,884,759 | A | | 3/1999 | Gueret | |
| 5,893,484 | A | | 4/1999 | Fuchs et al. | |
| 5,894,841 | A | | 4/1999 | Voges | |
| 5,910,138 | A | | 6/1999 | Sperko et al. | |
| 5,934,273 | A | * | 8/1999 | Andersson et al. | 128/203.12 |
| 5,944,217 | A | | 8/1999 | Baena | |
| 5,968,619 | A | | 10/1999 | Carmen et al. | |
| 6,013,363 | A | | 1/2000 | Takahashi et al. | |
| 6,062,213 | A | | 5/2000 | Fuisz et al. | |
| 6,062,430 | A | | 5/2000 | Fuchs | |
| 6,073,807 | A | | 6/2000 | Wilford et al. | |
| 6,109,315 | A | | 8/2000 | Stern | |
| 6,129,236 | A | | 10/2000 | Osokin et al. | |
| 6,158,676 | A | * | 12/2000 | Hughes | 239/405 |
| 6,223,933 | B1 | | 5/2001 | Hochrainer et al. | |
| 6,244,472 | B1 | | 6/2001 | Hennemann | |
| 6,250,508 | B1 | | 6/2001 | Geser et al. | |
| 6,280,431 | B1 | | 8/2001 | Domkowski et al. | |
| 6,286,700 | B1 | | 9/2001 | Davidson | |
| 6,303,152 | B1 | * | 10/2001 | Kief | 424/529 |
| 6,364,163 | B1 | | 4/2002 | Mueller | |
| 6,390,332 | B2 | | 5/2002 | Wakayama | |
| 6,685,691 | B1 | | 2/2004 | Freund et al. | |
| 6,846,413 | B1 | | 1/2005 | Kadel | |
| 6,918,547 | B2 | | 7/2005 | Jaeger et al. | |
| 6,932,789 | B2 | | 8/2005 | Zierenberg et al. | |
| 6,977,042 | B2 | | 12/2005 | Kadel | |
| 6,988,496 | B1 | | 1/2006 | Eicher et al. | |
| 7,040,311 | B2 | | 5/2006 | Hochrainer | |
| 7,645,383 | B2 | | 1/2010 | Kadel | |
| 7,819,342 | B2 | | 10/2010 | Spallek | |
| 7,837,235 | B2 | | 11/2010 | Geser | |
| 2001/0009151 | A1 | | 7/2001 | Hochrainer | |
| 2002/0007155 | A1 | | 1/2002 | Freund et al. | |
| 2005/0001076 | A1 | | 1/2005 | Eicher | |
| 2006/0016449 | A1 | | 1/2006 | Eicher et al. | |
| 2006/0239930 | A1 | | 10/2006 | Lamche | |
| 2009/0114215 | A1 | | 5/2009 | Boeck | |

FOREIGN PATENT DOCUMENTS

| | | | |
|---|---|---|---|
| DE | 3446697 | A1 | 6/1986 |
| DE | 0368112 | A2 | 10/1989 |
| DE | 19851404 | A1 | 5/2000 |
| EP | 0 114 964 | B1 | 8/1984 |
| EP | 0 169 501 | | 1/1986 |
| EP | 0 182 094 | B1 | 5/1986 |
| EP | 0 315 440 | B1 | 5/1989 |
| EP | 0368112 | A2 | 5/1990 |
| EP | 0 388 112 | B1 | 9/1990 |
| EP | 0 322 980 | B1 | 7/1992 |
| EP | 0 495 330 | A1 | 7/1992 |
| EP | 0 585 908 | A2 | 3/1994 |
| EP | 0 620 165 | B1 | 10/1994 |
| EP | 0 621 027 | B1 | 10/1994 |
| EP | 0 622 311 | A2 | 11/1994 |
| EP | 0 635 254 | B1 | 1/1995 |
| EP | 0 654 419 | A1 | 5/1995 |
| EP | 0 763 482 | A1 | 3/1997 |
| EP | 0653359 | B1 | 7/1997 |
| EP | 0812625 | | 12/1997 |
| EP | 0629165 | B1 | 4/1999 |
| FR | 2 762 589 | | 6/2001 |
| JP | 09-225356 | | 9/1997 |
| JP | 9-225356 | | 9/1997 |
| WO | WO 92/16439 | | 10/1992 |
| WO | WO 95/15895 | | 6/1995 |
| WO | WO 96/03218 | | 2/1996 |
| WO | WO 97/01329 | | 1/1997 |
| WO | WO 97/06842 | | 2/1997 |
| WO | WO 97/12687 | | 4/1997 |
| WO | WO 97/18143 | | 5/1997 |
| WO | WO 97/26998 | | 7/1997 |
| WO | WO 98/27959 | | 7/1998 |
| WO | WO 98/48943 | | 11/1998 |
| WO | 9907340 | A1 | 2/1999 |
| WO | WO 99/43571 | | 9/1999 |
| WO | WO 00/27543 | | 5/2000 |
| WO | WO 00/49988 | | 8/2000 |
| WO | 2007141201 | A1 | 12/2007 |
| WO | 2007141203 | A1 | 12/2007 |

OTHER PUBLICATIONS

English language Abstract of EP0585908, published Mar. 9, 1994, 1 page.

* cited by examiner

Fig.6
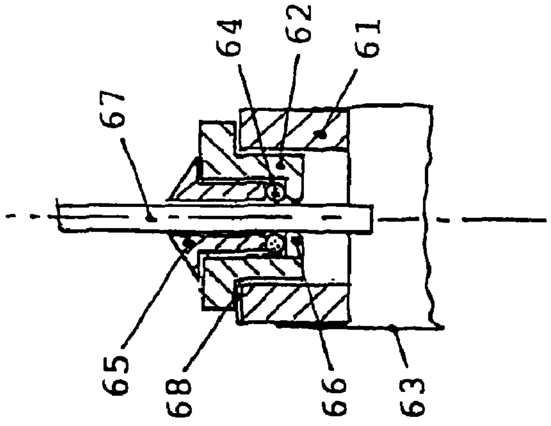
Fig.5a
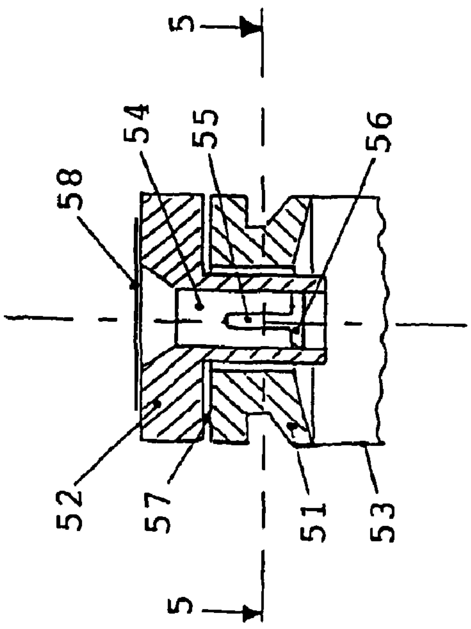
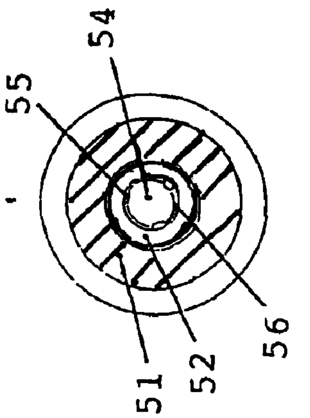
Fig.5b
Fig.4
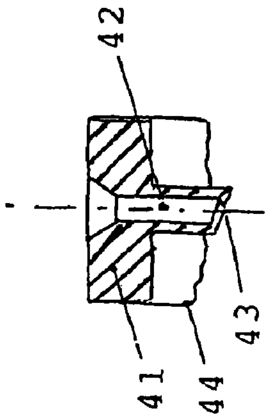

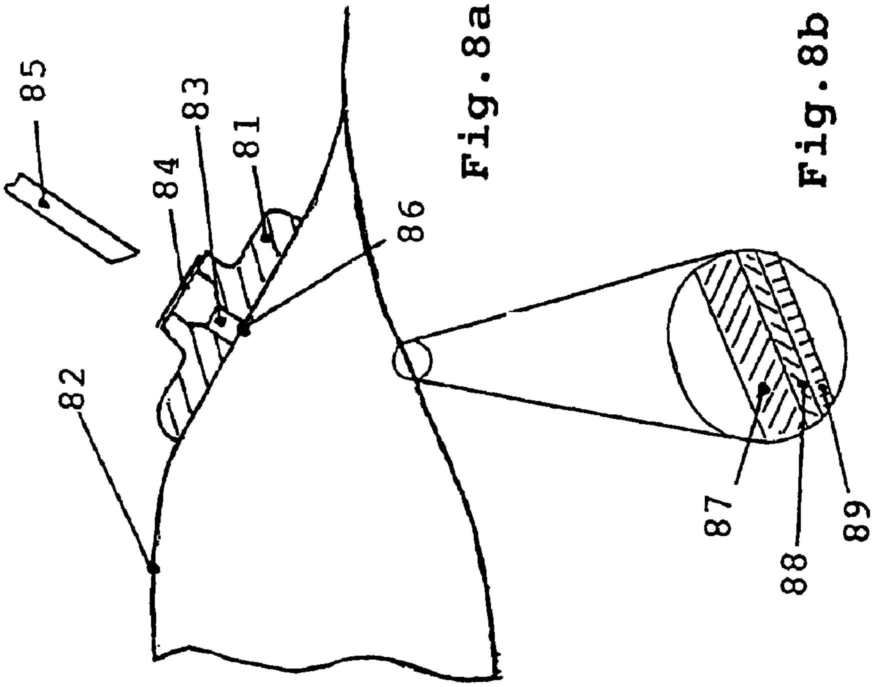
Fig.8a
Fig.8b
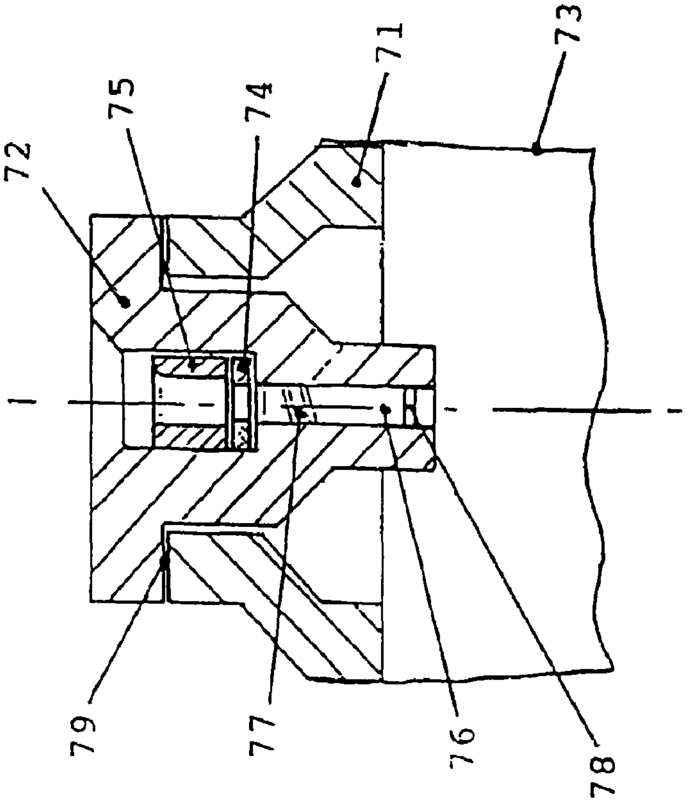
Fig.7

12g

12f

12e

12d

12c

12b

13f

13e

13d

13c

13b

CONTAINER FOR A MEDICINAL LIQUID

CROSS-REFERENCE TO RELATED APPLICATION

This application claims the benefit of Appl. No. 60/093,772, filed Jul. 23, 1998. This application is a divisional of application Ser. No. 09/258,357, filed Feb. 26, 1999. This application claims foreign priority benefits under 35 U.S.C. §119(a)-(e) to DE 198 08 295.9, filed Feb. 27, 1998.

BACKGROUND OF THE INVENTION

1. Field of the Invention

The present invention relates to a container for a medicinal liquid, more particularly to a container for a medicinal liquid, wherein the container is gas-tight and liquid-tight.

2. Related Art

EP-0 182 094 A2 sets forth a bottle-shaped pack comprising an outer container which is stiff in respect of shape and an inner container which is disposed in the outer container and which is in the form of an easily deformable bag for containing the filling material. The preform is produced by co-extrusion of two coaxial tubular portions. The two portions comprise two thermoplastic materials which are not joined together. The preform is expanded in a blow molding mold. A welded seam is provided at the flat bottom of the inner container. The flat bottom which is formed on the outer container has an opening in the form of a slot. The outer container and the inner container are connected together in a positively locking relationship in the region of the discharge opening. That pack is produced substantially in one working operation.

The filling material is discharged from the container by means of a pump which is disposed in the discharge opening. The pump causes the inner container to deform as its volume decreases. Air passes into the space between the outer container and the deformed inner container, through the open slot in the flat bottom of the outer container, thereby preventing the occurrence of a reduced pressure in that intermediate space. The inner container does not involve a fixed contact with respect to the outer container, except in the region of the discharge opening. The pack can be provided with a dip tube which extends almost as far as the flat bottom and which holds the inner container in the extended condition. That pack can be satisfactorily used and completely emptied, only when it is in a given position in space.

A tubular bag of composite foil is described in EP-0 620 165 A1. The composite foil comprises at least an outwardly disposed plastic foil and an inwardly disposed metal foil. The tubular bag is closed at both ends in a sack-like configuration. The bag is provided with a desired-rupture location, by means of which it can be reliably opened at that point. A tubular bag of that kind serves to store a hardenable material which is expelled from the tubular bag by means of an expelling device.

EP-0 068 653 A1 describes a flexible and collapsible container which is intended for one-trip use and which is made from a foil and which is used in a suction or feeding bottle which can be used a plurality of times. The one end of the container is open while the other end is closed by means of a welded seam and provided with a tongue portion. The tongue portion is clamped in a gap provided at the bottom of the suction or feeding bottle. That provides that the bag-like container is constantly held in an extended condition in the suction or feeding bottle.

SUMMARY OF THE INVENTION

The invention aims to make the production of a container which is intended for one-trip use more economical without adversely affecting its usefulness, and to simplify handling thereof.

The object of the present invention is to provide a container for a medicinal liquid, which is gas-tight and liquid-tight, and which has a filling volume that is suited to the intended purpose of use. The container plastically and irreversibly collapses under a slightly reduced pressure in a predetermined manner such that it can be substantially emptied.

The container of the present invention includes a foil bag which is closed at both ends. At a differential pressure between the interior of the container and its surroundings below 300 hPa (300 mbar), the foil bag is deformable by the external pressure and collapses. The container further includes a flange which is stable in respect of shape and which is sealingly mounted to the foil bag. The flange is a releasable connecting element for fitting the container on to a discharge connection member.

The foil bag is closed at at least one end with at least one welded seam which extends substantially transversely with respect to the axis of the bag. The flange has a sealing location which is stable in respect of shape. A discharge location for the liquid in the region of the flange is also provided, the discharge location being is stable in respect of shape.

The container of the present invention has several advantages over conventional containers. For example, the container of the present invention is economical to produce, is suitable for one-trip use and requires only a small amount of material usage.

Further, the container of the present invention can be produced in a sterile condition and filled and sealed in a sterile condition. It can also be used for medicaments intended for inhalation, which are typically provided as solutions in ethanol, water, or an ethanol and water mixture.

The liquid is discharged from the container of the present invention under sterile conditions, such that no air is sucked into the container upon discharge. As such, the liquid does not come into contact with air, oxygen or carbon dioxide.

Further, the container of the present invention permits gas and bubble-free discharge of the medicinal liquid.

The container of the present invention is sealed so that diffusion of liquids and gases is minimized. The container can be filled and then stored over several years, depending on the particular medicament involved, and still satisfy the requirements of all official pharmacopoeiae.

The container is easily deformable at a slightly reduced pressure. Further, in the collapsed condition the container of the present invention remains flat and stretched out, such that it retains its initial length after emptying.

Further, the container of the present invention does not require a valve for pressure equalization after a portion of the liquid has been discharged, and the container can be substantially emptied, even in a fluctuating position and when it is upside down.

The foil bag of the present invention is connected only to the flange which is stable in respect of shape and is not fixed to any casing, if such is provided.

The filling volume of the container can be easily adjusted to a predetermined value within a certain range by changing the length and/or the diameter of the foil bag. Further, the container can be filled prior to closure, before the single or the second welded seam is produced. As such, there is no need for a separate closure means.

The container can be used with or without a casing. If the container is disposed in a casing, it is protected from external damage.

The liquid is stored in the container of the present invention such that it is protected from the effect of light by an opaque foil bag or by an opaque casing which is closed all around.

Further, the container of the present invention can be fitted into and removed from a discharge device in a simple fashion and without rotary movement.

BRIEF DESCRIPTION OF THE FIGURES

The foregoing and other features and advantages of the invention will be apparent from the following, more particular description of a preferred embodiment of the invention, as illustrated in the accompanying drawings.

FIG. 4 is a sectional view of a first embodiment of a flange of the present invention.

FIG. 5*a* is a sectional view of a second embodiment of a flange of the present invention.

FIG. 5*b* is a sectional view of the second embodiment of the flange taken along a line 5-5 of FIG. 5*a*.

FIG. 6 is a sectional view of a third embodiment of a flange of the present invention.

FIG. 7 is a sectional view of a fourth embodiment of a flange of the present invention.

FIG. 8*a* is a view of a one-part flange of the present invention, which is disposed on the side of a foil bag.

FIG. 8*b* is an exploded view of a cross-section of laminate foil used to make up the foil bag of FIG. 8*a*.

FIGS. 12*a*-12*g* show a series of perspective views of manufacturing and filling of a container according a first embodiment of the present invention.

FIGS. 13*a*-13*f* show a series of perspective views of manufacturing and filling of a container according a second embodiment of the present invention.

DETAILED DESCRIPTION OF THE PREFERRED EMBODIMENTS

Figure 3:
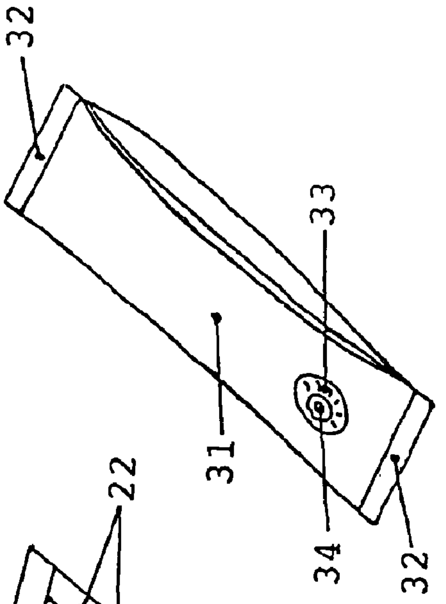
FIG. 3 is a perspective view of a third embodiment of a foil bag of the present invention which is closed at both ends.

A preferred embodiment of the present invention is now described with reference to the figures where like reference numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

The object of the present invention is to provide a container for a medicinal liquid, which is gas-tight and liquid-tight, and which has a filling volume that is suited to the intended purpose of use. The container plastically and irreversibly collapses under a slightly reduced pressure in a predetermined manner such that it can be substantially emptied.

The container of the present invention includes a foil bag which is closed at both ends. At a differential pressure between the interior of the container and its surroundings below 300 hPa (300 mbar), the foil bag is deformable by the external pressure and collapses. The container further includes a flange which is stable in respect of shape and which is sealingly mounted to the foil bag. The flange is a releasable connecting element for fitting the container on to a discharge connection member.

The foil bag is closed at at least one end with at least one welded seam which extends substantially transversely with respect to the axis of the bag. The flange has a sealing location which is stable in respect of shape. A discharge location for the liquid in the region of the flange is also provided, the discharge location being is stable in respect of shape.

In a further embodiment, the collapsible foil bag can be deformed by and collapsed due to an external pressure at a differential pressure of below 150 hPa (150 mbar) or preferably below 80 hPa (80 mbar).

The foil bag can be closed by a welded seam at both ends. In that case, the flange, which is stable in respect of shape, is sealingly welded to the side of the foil bag, preferably in the proximity of one end of the foil bag. The foil bag, however, may also be sealingly closed at one end by a welded seam and at the other end by the flange. In this case, the one end of the foil bag is welded to the flange, preferably on the periphery thereof.

The foil bag can be made of a tube which does not have a welded seam extending in the axial direction of the foil bag. In an alternate embodiment, the foil bag may have one or two welded seams extending in the longitudinal direction. The foil bag can be in the form of a flat bag or a bag with side folds. A bag with a welded seam extending in the longitudinal direction is preferred.

In one embodiment, the foil bag is made of a foil of metal or metal alloy, preferably aluminum, gold or copper, or plastic material, preferably a thermoplastic material. In another embodiment, the foil bag is made of a composite foil of plastic material and metal. The composite foil preferably comprises two or three foils which are joined together. The foil bag may further comprise a plastic foil to which a layer of metal, glass or ceramic is applied, for example by vapor deposition. The foils of plastic material or metal are several micrometers thick. The thickness of the vapor-deposition layers of metal, glass or ceramic is in the sub-micrometer range.

A composite foil consisting of two foils can be made of a metal foil and a plastic foil which are joined together. In this embodiment, the metal foil forms the inward side or the outward side of the composite foil. In another embodiment, the composite foil comprises two different plastic foils.

The composite foil comprising three foils preferably comprises two plastic foils, between which there is a foil comprising metal. All three foils are joined together. In place of the metal foil, the composite foil may have a layer of glass or ceramic, for example of silicon oxide ($SiO_x$), which is produced by vapor deposition on a plastic foil.

In a further embodiment the inner foil of the composite foil comprises a copolymer, for example a polyethylene copolymer of ethylene-acrylic acid. The outer plastic foil of the composite foil is preferably a plastic material, for example polyethylene terephthalate, the melting temperature of which is higher than the melting temperature of the plastic material of the inner foil. That facilitates seam-wise welding of the plastic material of the inner foil, in the production of the foil bag.

In the composite foil, a bonding layer may possibly be provided between two foils.

The foil bag can comprise a plastic foil of a thickness of between 20 μm and 100 μm. It may also comprise a composite foil with an inner foil of plastic material of a thickness of between 20 μm and 100 μm and an outer foil of metal of a thickness of between 8 μm and 20 μm. It may also comprise a composite foil with an inner foil of plastic material of a thickness of between 20 μm and 100 μm, a central foil of metal of a thickness of between 8 μm and 20 μm and an outer foil of plastic material of a thickness of between 10 μm and 40 μm.

The container according to the invention is described in greater detail with reference to the Figures by way of example.

Figure 2:
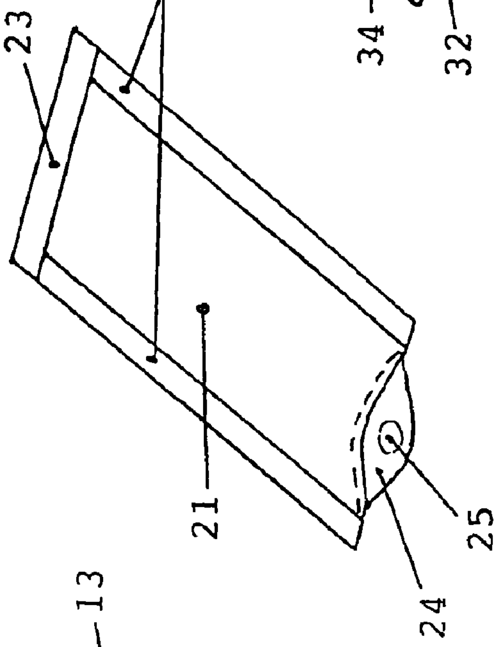
FIG. 2 is a perspective view of a second embodiment of a foil bag of the present invention which is closed at both ends.
Figure 1:
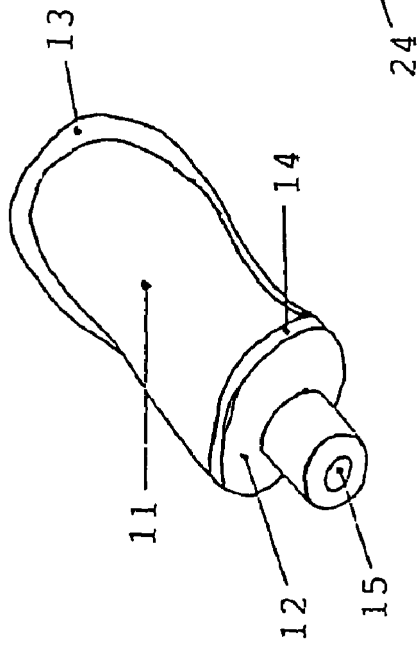
FIG. 1 is a perspective view of a first embodiment of a foil bag of the present invention which is closed at both ends.

FIGS. 1 to 3 are perspective views of various embodiments of the foil bag which is closed at both ends. FIG. 1 shows a tubular bag 11 with a cylindrical flange 12 which is stable in respect of shape, and a U-shaped transverse seam 13 which closes the one end of the tubular bag and which at least partially extends in the longitudinal direction thereof. The edge 14 of the flange is connected to the other end of the tubular bag. Disposed on the axis of the flange is a hole 15 into which a discharge connection member can be introduced.

FIG. 2 shows a sealed-edge bag (21) which comprises two foils which are disposed one upon the other. It has two welded seams 22 extending in the longitudinal direction of the bag and, at its one end, a welded seam 23 extending in the transverse direction. The other end is connected to a flange 24 which is stable in respect of shape and which is of a fish-like form. Disposed at the center of the flange is a hole 25 into which a discharge connection member can be inserted.

FIG. 3 shows a side fold bag 31 with folds at both longitudinal sides, which is closed at each of its two ends by a respective transversely extending welded seam 32. The flange 33 which is stable in respect of shape is welded on to the bag on a flat side thereof. A discharge connection member can be inserted into the hole 34 of the flange.

The flange which is stable in respect of shape can be of different shapes. If it is disposed at the end of the foil bag as the closure means thereof, it can be of a rotationally symmetrical form and can be adapted to the size of the end of the foil bag. The flange can also be provided with a guide passage into which the discharge connection member can be introduced. The discharge connection member is disposed within this guide passage when the container is fit thereon.

In one embodiment, the guide passage is provided with a press fit which embraces the discharge connection member. In one embodiment, the press fit is a portion of the guide passage which comprises a smooth inside wall of an inside diameter which only slightly differs from the outside diameter of the discharge connection member. In a further embodiment, a plurality of bulge portions can be provided in a portion of the guide passage on the inside wall thereof. The bulge portions can be for example three bulge portions which are of an elongate configuration and which are arranged symmetrically extending in the axial direction. It is further possible to provide a plurality of bulge portions which are arranged at an axial spacing from each other and which extend in the azimuthal direction and which for example form two rings or which comprise a plurality of ring portions. Furthermore, the bulge portions can extend in a helical configuration, such that they can comprise a plurality of helix portions distributed on the inside wall of the guide passage or a helix portion whose length is greater than the periphery of the guide passage. A press fit of that kind permits the container to be fitted on to the discharge connection member and can provide for a sufficiently firm fit of the flange on the discharge connection member. Furthermore, after it has been emptied, the container can be withdrawn from the discharge connection member without damaging the latter.

The flange can be in one or more parts. A multi-part flange is preferably a two-part flange. An outwardly disposed part of the flange is sealingly connected to the foil bag. The outer part contains an opening which is sealingly closed with the inner part. The two parts can be screwed together by means of a screwthread or can be connected together by means of a snap-action connection or by ultrasonic welding. A one-part flange is of a similar configuration to the two-part flange, but it does not include any connecting elements. The flange can be produced at the same time with a press fit, a groove for the sealing location, and a pierceable membrane.

The flange can be made of rubber, metal or plastic material, preferably a thermoplastic material. It may be desirable to produce the flange from the same plastic material as that used to form the foil bag or the inward side of the foil bag. A flange which is made of rubber or metal can be connected to the foil bag by gluing or possibly by vulcanization.

FIGS. 4 to 7 are sectional views of various embodiments of the flange. FIG. 4 is a view in longitudinal section through a one-piece flange 41 having a cylindrical guide passage 42, which is in the form of a press fit, for a cylindrical discharge connection member. The outer end of the guide passage is beveled while the other end is closed by a membrane 43 which is disposed at an incline to the axis of the flange. Flange 41 is produced in one working operation. The edge of flange 41 is connected to a foil bag 44.

FIG. 5*a* shows a longitudinal section through a multi-part cylindrical flange, and FIG. 5*b* shows a cross-section taken along a line 5-5 of FIG. 5*a*. A lower part 51 of the flange is connected to a foil bag 53. An upper part 52 of the flange fits in an opening in lower part 51. Upper part 52 is provided with a guide passage 54 in which there are three elongate ridges 55, as shown in FIG. 5*b*, extending in the axial direction of the flange. The elongate ridges 55 act as a press fit for a discharge connection member. An annular ridge 56 acts as a seal. Lower part 51 and upper part 52 are welded together at their contact surface 57. Guide passage 54 has an entry opening with an inclined insertion surface. This entry opening is sealed off by a sealing foil 58.

FIG. 6 shows a multi-part cylindrical flange which is stable in respect of shape. A lower part 61 of the flange is connected to a foil bag 63. An upper part 62 of the flange projects into the annular lower part 61. Disposed in upper part 62 as a seal is an O-ring 64 which is held in place by a gland 65 that is pressed into position. The opening in gland 65 serves as a guide passage for a discharge connection member. A peripherally extending ridge 66 is disposed on the inside of the seal on upper part 62, which provides a press fit. A discharge connection member 67 is inserted into the guide passage of gland 65. The container is held on discharge connection member 67 by means of peripherally extending ridge press fit 66. Lower part 61 and upper part 62 are welded together at their contact surface 68.

FIG. 7 shows another embodiment of a multi-part flange of the present invention. A lower part 71 of the flange is connected to a foil bag 73. An upper part 72 of the flange is disposed in the annular lower part 71 which is provided with a shoulder. Upper part 72 includes a flat ring 74 as a seal, which is held in place by a gland 75 which is pressed into position. A guide passage 76 for a discharge connection member is disposed beneath flat ring 74. A press fit is formed by two ridges 77 within guide passage 76, extending therearound in a screwthread-like configuration. A membrane 78 is provided in the proximity of the lower end of guide passage 76 and perpendicular to the axis of the flange. Membrane 78 is pierced when the container is fit onto the discharge connection member. Membrane 78 is produced with upper part 72 in one working operation. Lower part 71 and upper part 72 are connected together at their contact surface 79.

FIG. 8*a* is a view in cross-section of a one-part flange 81 which is stable in respect of shape and which is disposed on the side of a foil bag 82. Flange 81 has a guide passage 83 which serves as a press fit for a discharge connection member. Flange 81 is sealed on its outward side by a sealing foil 84. When the container is fitted on to a discharge connection member 85, having a beveled end, the foil bag is pierced at an inner end 86 of guide passage 83.

FIG. 8*b* shows an exploded view in cross-section through a commercially available laminate foil having three layers making up the foil bag. An inner foil 87 comprises polyethylene (40 μm in thickness), a central foil 88 acts as the diffusion barrier of aluminum (12 μm in thickness) and an outer foil 89 comprises polyethylene terephthalate (12 μm in thickness).

The welded seam at one or both ends of the foil bag can be of a U-, V- or T-shaped configuration. The seam extends substantially transversely with respect to the axis of the bag. In one embodiment, the welded seam extends partially in the direction of the axis of the bag, whereby the defined deformation of the foil bag is promoted when liquid is drawn therefrom.

A sealing location or sealing means can be provided within or at one of the ends of the guide passage. The sealing location can comprise a ring which is disposed in a groove provided on the inside wall of the guide passage. The ring can be of an O-shaped or substantially rectangular cross-section. The ring may be provided with a sealing lip. The ring is made of an elastomer, a thermoplastic elastomer or rubber. The sealing location closes the filling space or chamber of the container which is fitted on to the discharge connection member gas-tightly and liquid-tightly in relation to the ambient air. Further, the sealing location permits the emptied container to be withdrawn from the discharge connection member. The sealing location is required if the sealing effect of the press fit is not sufficient.

The welded seams on the foil bag can be from 0.7 mm to 3 mm wide. The width of the welded seams is selected in accordance with the requirements for sealing integrity and durability of the seam. Wide, longitudinal seams on the foil bag can be bent over after the welding operation so that they are disposed on the outside against the foil bag and so that the foil bag is only a little wider than its width in the unwelded part between the welded seams.

The welded seams on the foil bag and the weld location between the foil bag and the flange are produced using known processes such as thermal welding, ultrasonic welding or induction welding in the case of composite foils with a metal layer, wherein the weld locations are preferably pressed together in the heated condition. Such processes are set forth for example in EP-0 111 131 and EP-0 130 239, the disclosures of which are incorporated herein by reference in their entireties.

Figure 11A:
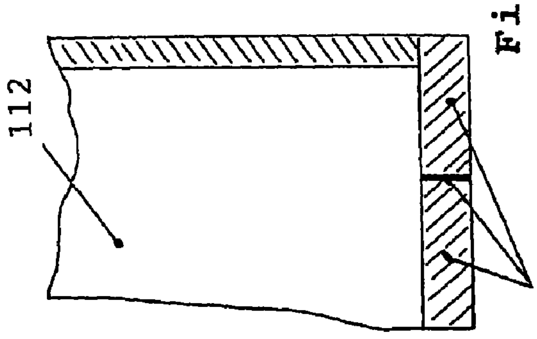
FIG. 11*a* is a side view of a third embodiment of the welded seam of the present invention.
Figure 11B:
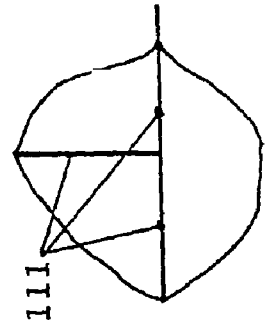
FIG. 11*b* is a plan view of the welded seam of FIG. 11*a*.

FIGS. 9*a*, 9*b*, 10*a* and 10*b* show cross-section and side views of various embodiments of the welded seam with which the foil bag is closed at at least one end. FIGS. 11*a* and 11*b* show a side view and plan view of an alternate embodiment of the welded seam on the end of the bag.

Figure 9A:
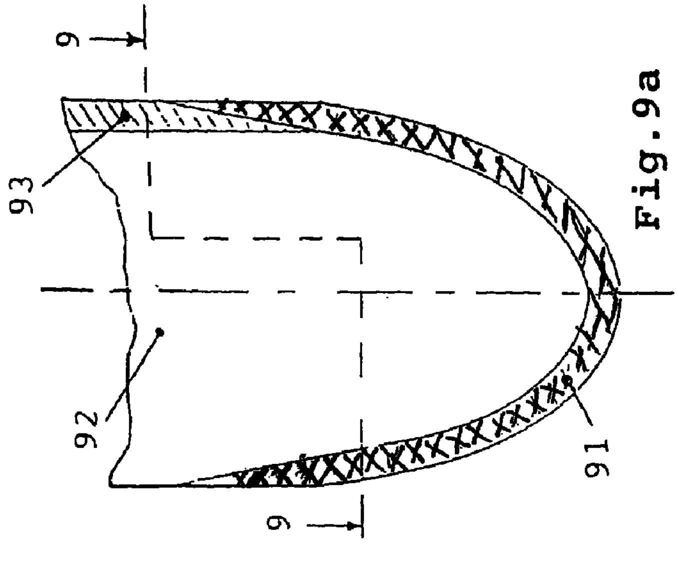
FIG. 9*a* is a side view of first embodiment of a welded seam of the present invention.
Figure 9B:
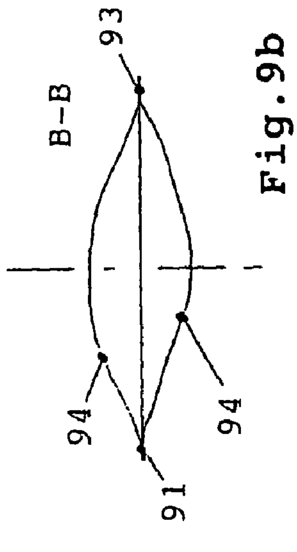
FIG. 9*b* is a sectional view of the welded seam taken along a line 9-9 of FIG. 9*a*.

FIG. 9*a* shows a U-shaped welded seam 91 which extends partially in the longitudinal direction of a foil bag 92. On one side of foil bag 92, welded seam 91 merges with a welded seam 93 of the foil bag, with the welded seam 93 extending in the longitudinal direction. FIG. 9*b* is a view in cross-section through the foil bag taken along a line 9-9 of FIG. 9*a*. The inner layer of the folded multi-layer foil 94 is welded in welded seams 91 and 93.

Figure 10A:
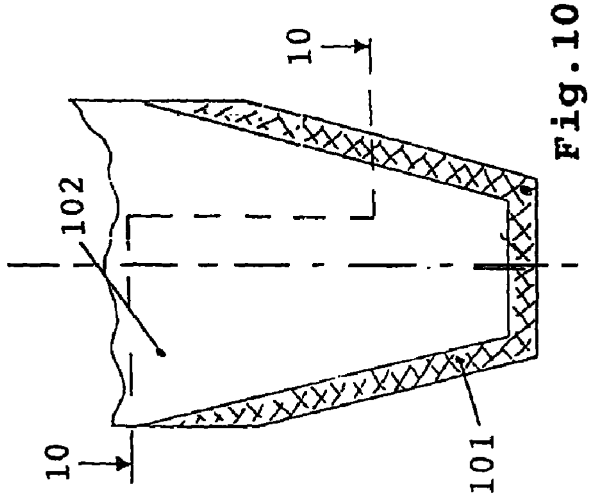
FIG. 10*a* is side view a second embodiment of a welded seam of the present invention.
Figure 10B:
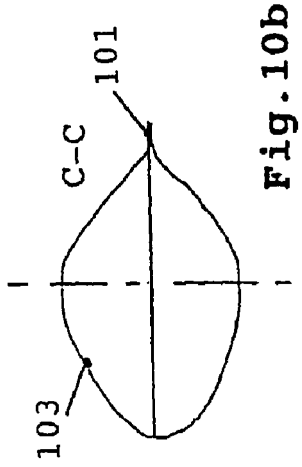
FIG. 10*b* is a sectional view of the welded seam taken along a line 10-10 of FIG. 10*a*.

FIG. 10*a* shows a V-shaped welded seam 101 which extends partially in the longitudinal direction of a foil bag 102. In this case foil bag 102 comprises a tubular foil without a longitudinal seam. FIG. 10*b* shows a view in cross-section through the foil bag taken along a line 10-10 of FIG. 10*a*. The folded single-layer foil 103 is welded in welded seam 101.

FIG. 11*a* shows a T-shaped welded seam 111 as a side view, and FIG. 11*b* is a plan view of the welded end of a foil bag 112. The three limbs of the T-shaped seam 111 are overall as long as the foil bag is wide, when the foil bag 112 is collapsed flat, outside the T-shaped seam.

A foil bag which is welded with a U-, V- or T-shaped seam is no greater in the region of the transverse seam than the diameter of the casing into which the foil bag is possibly inserted.

The discharge location is preferably in the form of a puncture or perforation location. A pierceable membrane can be provided at the puncture or perforation location, the membrane being pierced when the container is fitted on to the discharge connection member. The membrane is preferably arranged between the sealing location and the liquid chamber or space in the foil bag. The pierceable membrane can be disposed at one of the ends or within the guide passage. It is preferably disposed directly at the end of the guide passage or in the proximity of that end which is towards the liquid space. It can be a part of the flange or a part of the foil bag. If it is a part of the flange, it can be produced at the same time as the flange, and can be made of the same plastic material as the flange. The pierceable membrane acts as an original closure means for the filling space or chamber in the foil bag.

In a further embodiment the discharge location can be sealed with a sealing foil which is pulled off before the container is fitted on to the discharge connection member or which is pierced when the container is fitted on to the discharge connection member.

The container may be disposed in a casing which is stable in respect of shape, and which is made of metal or plastic material. One end of the casing is releasably or non-releasably connected to the flange, while the other end of the casing may be closed with a bottom. In one embodiment, the casing is substantially closed all around, however, it includes at least one opening. Alternatively, a gap may be provided at the location of connection of the casing to the flange. The casing can also be in the form of a basket which is stable in respect of shape and which has many openings. In an alternate embodiment, instead of the casing, the container may be disposed in a U-shaped holder which is stable in respect of shape, wherein the end of each limb of the U-shaped holder is secured to the flange, and the limbs are longer than the foil bag.

In a preferred embodiment, the container disposed in a casing is connected to the casing only at the flange. The end which is closed with a welded seam or the two ends of the foil bag, which are closed with a welded seam, are not connected to the casing.

Upon the transfer of liquid out of the container into the discharge connection member the foil bag collapses flat due to the action of the external pressure. Air passes through the opening in the casing or through the gap between the casing and the flange, into the space between the casing and the foil bag, and provides for pressure equalization. As such, no valve is required in the foil bag and the liquid in the foil bag does not come into contact with air.

Manufacture and filling of the container according to the invention is diagrammatically illustrated in perspective views in FIGS. 12*a*-12*g* and 13*a*-13*f.*

Figure 12A:
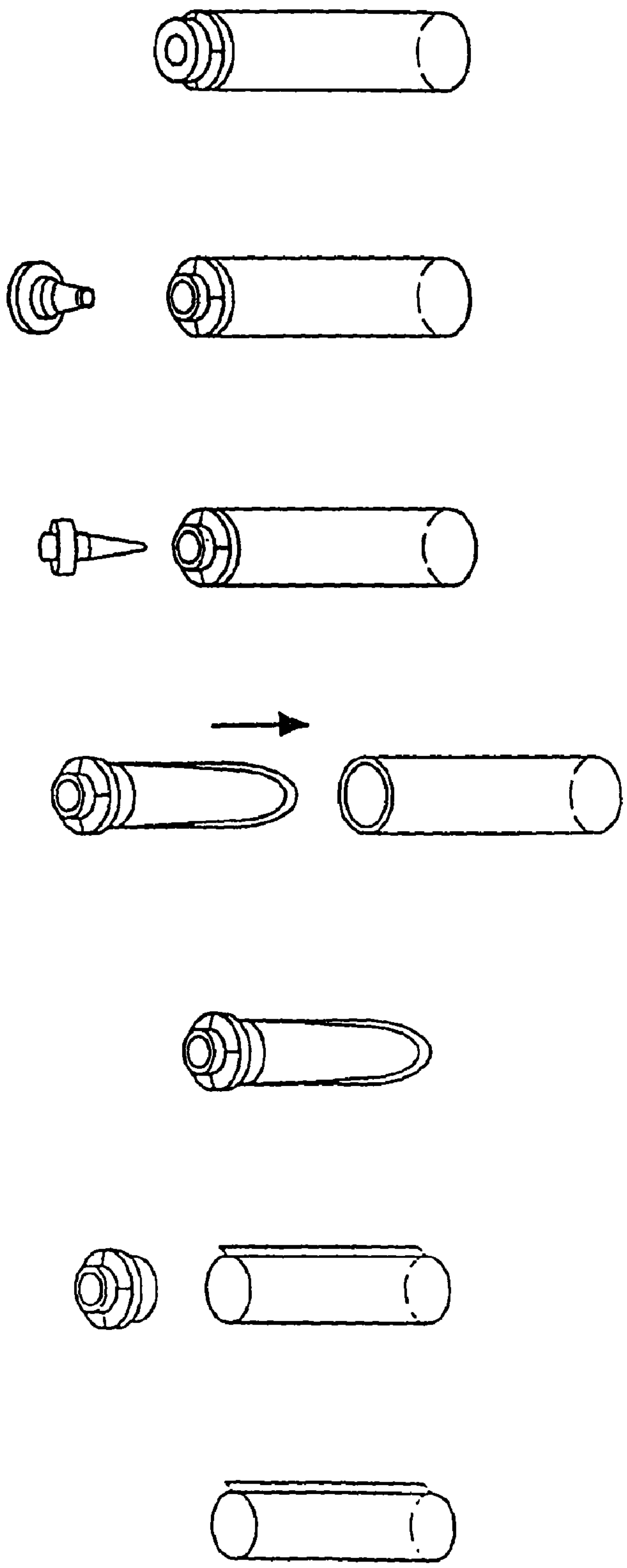

As shown in FIG. 12*a*, a folded foil strip is provided at the cut sides with a welded seam in the longitudinal direction, divided into portions and shaped to form a tube. The lower part of a two-part cylindrical flange, which is produced by an injection molding process, is welded to one end of the tub, as shown in FIG. 12*b*. The other end of the tube is welded with a U-shaped transverse seam as shown in FIGS. 12*c*. The finished container is pushed into a cylindrical casing of aluminum, as shown in FIG. 12*d*, the edge of which is pressed into a groove or channel in the edge of the cylindrical flange. The container is fixedly joined to the casing in that way. The empty container which is disposed in the casing is then filled with a fluid through the lower part of the flange, which is provided with an opening, as shown in FIG. 12*e*. After the filling operation the upper part of the flange is pressed into the lower part, as shown in FIG. 12*f,* and the two parts are sealingly joined together. The finished part, as shown in FIG. 12*g*, is ready for being fit onto a discharge connection member.

Figure 13A:
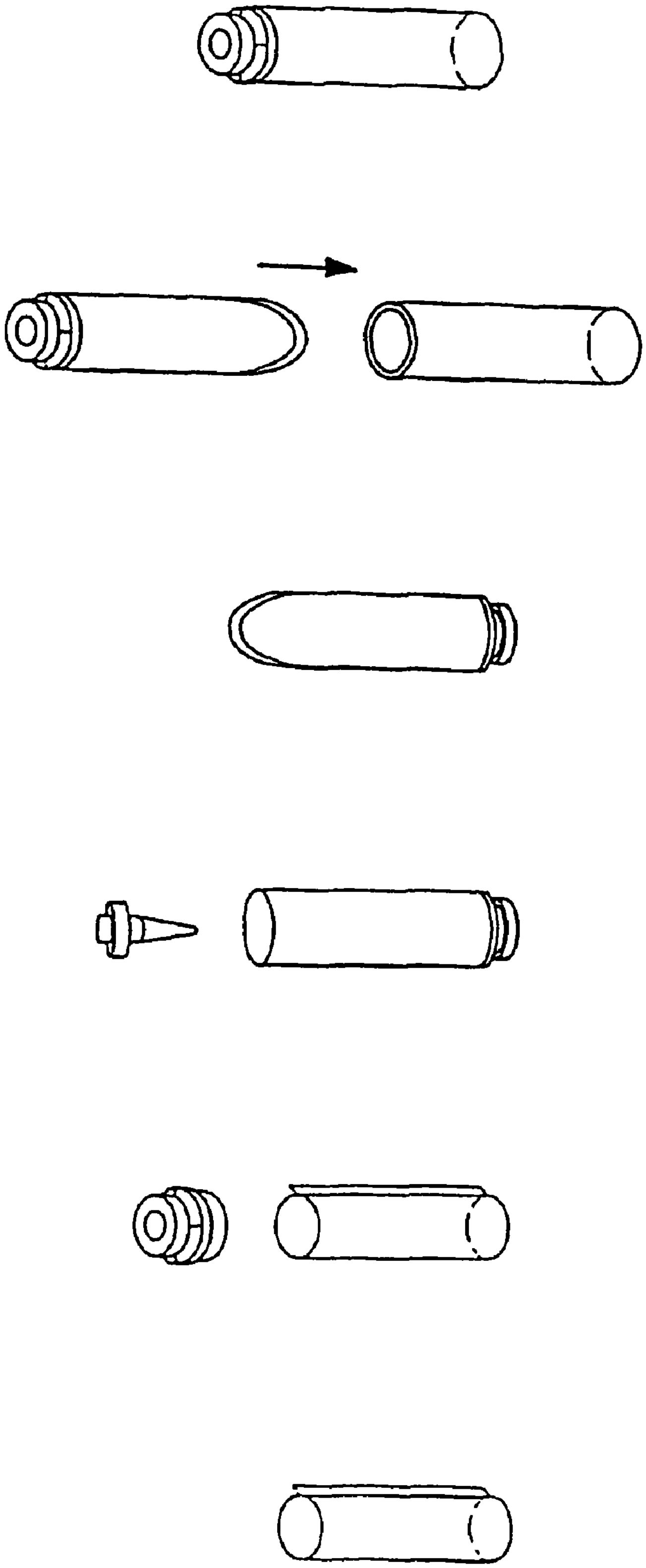

An alternate production process is illustrated in FIGS. 13*a*-13*f.* A portion of a foil tube is provided with a longitudinal seam, as shown in FIG. 13*a*. The tube is connected at one end to a one-piece flange which is closed by a sealing foil, as shown in FIG. 13*b*. The container is filled with a fluid through the other open end of the foil tube, as shown in FIG. 13*c*. The open end of the foil tube is closed by a U-shaped transverse seam, as shown in FIG. 13*d*. The filled container is fit into a casing of plastic material, as shown in FIG. 13*e*. The edge of the plastic casing is snap-fit onto the edge of the one-piece flange. The finished part, as shown in FIG. 13*f,* is ready for being fit onto a discharge connection member.

Figure 14:
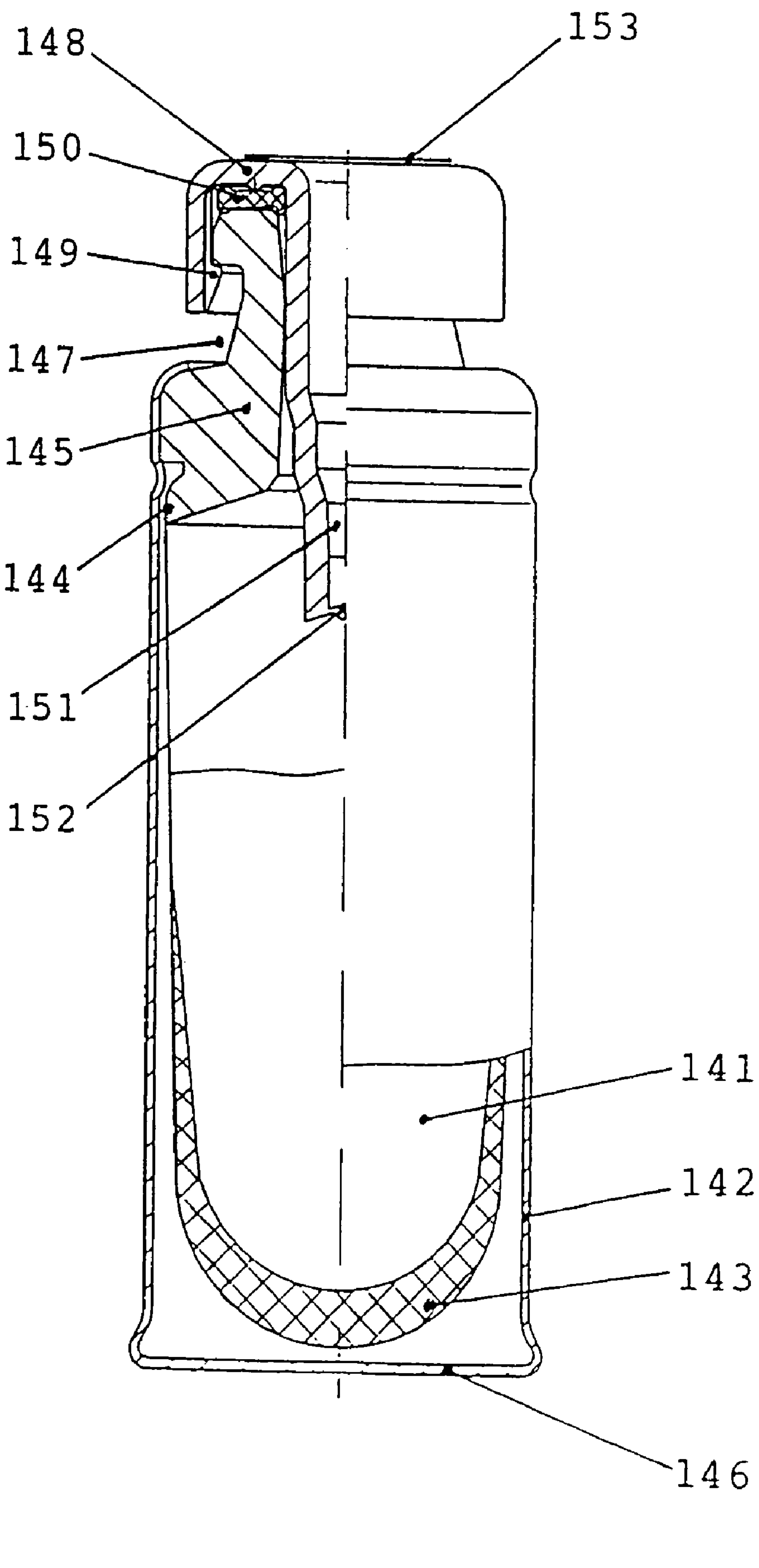
FIG. 14 is a partial sectional view of a container according to the present invention.

FIG. 14 is a partly cross-sectional view of a typical container 141 according to the present invention which is filled with a fluid and which is disposed in a metal casing 142. At one end, a foil bag is welded by a U-shaped seam 143. At its other end, the foil bag is welded to an edge 144 of a lower part 145 of a two-part cylindrical flange which is stable in respect of shape. Metal casing 142 has a bottom 146 in which there is a hole formed therein, through which air can pass into the space between metal casing 142 and the foil bag. The open end of metal casing 142 is pressed into a groove or channel 147 in the edge of lower part 145 of the flange. Metal casing 142 is fixedly connected to the flange. An upper part 148 of the flange is fit into an opening in lower part 145. Lower part 145 and upper part 148 are connected by a snap-action closure 149 and provided with a flat seal 150. A guide passage 151 is closed at its inner end by a membrane 152 and sealed at its outer end by a sealing foil 153.

The metal casing shown in FIG. 14 is preferably made of aluminum. In one embodiment, it is 43 mm in length and has an outside diameter of 17 mm and a wall which is 0.5 mm in thickness. The two-piece flange is preferably made of polyethylene and is produced by an injection molding process. The upper part of the flange including the membrane is preferably produced in one step in the process. The guide passage in the upper part of the flange preferably has an inside diameter of 2.5 mm at the location of the press fit and fits firmly onto a discharge connection member.

The foil bag is diffusion-tight with respect to the medicinal liquid and its constituents and with respect to gases. The material for the foil bag and possibly the structure of the composite foil are suitably selected for use with the liquid. Diffusion-tight in accordance with the present invention denotes a loss of liquid (measured with ethanol at ambient temperature) of the container due to diffusion of less than 0.6 mg per day, preferably less than 0.4 mg per day, particularly preferably less than 0.2 mg per day, in particular less than 0.1 mg per day.

The inner foil or the inward side of the foil bag is in contact with the liquid introduced into the bag. The material adopted for that foil is a material which is not attacked by the liquid and which does not adversely affect the liquid. That foil is preferably in the form of a weldable foil.

One of the foils or a layer which is applied for example by vapor deposition is the diffusion barrier. This barrier prevents diffusion of the liquid or the constituents thereof and prevents the diffusion of gases from or into the foil bag. It may be desirable to protect the diffusion barrier from mechanical damage and from tearing when the foil is bent. One method of protection is to apply a further plastic foil to the diffusion barrier so that the diffusion of liquid or gases remains durably prevented.

As the foil bag is diffusion-tight in relation to gases, the reduced pressure which occurs in the foil bag due to the discharge of liquid therefrom cannot be compensated by gas diffusing therein. As such, the foil bag reliably collapses even when liquid is very slowly discharged from the container. The liquid can also be drawn from the foil bag in a large number of partial quantities, for example 200 metered amounts, distributed over a prolonged period of time, for example three months.

The container, which is disposed in a substantially closed casing, is inaccessible from the exterior and cannot be damaged when stored or when it is fit onto the discharge connection member. The substantially closed casing, the casing which is provided in the form of a basket with many openings, or the holder which is stable in respect of shape facilitates storage of the container with the thin-gauge foil bag. These casings also facilitate handling thereof when it is fit onto the discharge connection member and when the empty container is withdrawn from the discharge connection member.

One example of a discharge connection member is the hollow plunger of an atomizer for medicinal liquids. An atomizer of that kind is described in DE-195 36 902.5 and in WO-97/12687, the disclosures of which are incorporated herein by reference in their entireties. An exemplary atomizer is shown in FIGS. 6*a* and 6*b* of these disclosures. The hollow plunger of the atomizer is in the form of a discharge connection member for the medicinal liquid contained in the container according to the invention. The container is fit onto the hollow plunger which is preferably disposed on the axis of the atomizer. In such a configuration, the end of the hollow plunger sticks into the discharge location and thus dips into the medicinal liquid. The sealing location in the flange sealingly closes off the interior of the container relative to the outside wall of the hollow plunger. The press fit holds the container sufficiently mechanically fast on the hollow plunger.

It may be desirable instead of or in addition to the press fit (force-locking connection) between the container and the discharge connection member to provide a releasable, positively locking connection between the flange which is stable in respect of shape of the container and the discharge device, for example an atomizer. A connection of that kind can be in the form of a push-in snap connection comprising a plurality of snap hooks which are mounted in a connecting portion in the discharge device. When the container is fit onto the discharge device the snap hooks engage into an opening in the flange, for example into a peripherally extending groove or behind an edge of the flange. The snap noses are preferably of a round shape or are beveled in both directions of movement of the container so that an empty container can be removed with the application of a moderate amount of force and a full container can be fit onto the discharge device with a moderate amount of force.

Figure 15A:
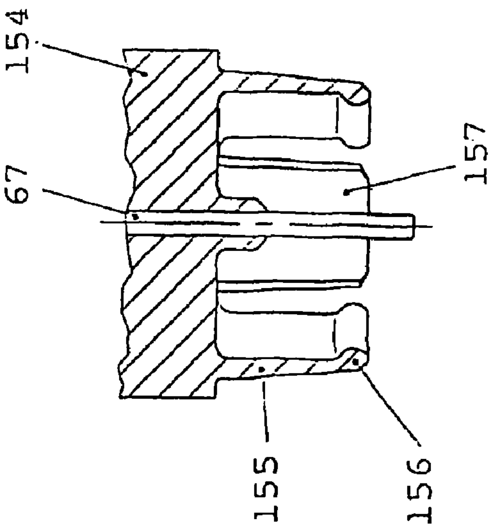
FIG. 15*a* is a sectional view of a first embodiment of a connecting portion of a container of the present invention.
Figure 15B:
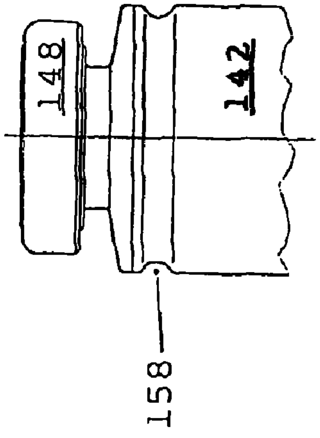
FIG. 15*b* is a side view of one end of the container of FIG. 15*a*.

FIGS. 15*a* and 15*b* show a releasable, positively locking, push-in snap connection between the flange which is stable in respect of shape of the container and the connecting portion in a discharge device.

FIG. 15*a* is a view in cross-section through a connecting portion 154 which is disposed in the discharge device and which on its axis includes discharge connection member 67. Discharge connection member 67 is surrounded by a plurality of snap hooks 155 with snap noses 156 of round cross-section. Snap hooks 155 are separated from each other by intermediate spaces and may involve an azimuthal width of 10 degrees to 60 degrees. A portion 157 which does not include any snap nose can be provided between two snap hooks 155. Portion 157 bears in positively locking relationship against the outside wall of the inserted container.

FIG. 15*b* is a side view of the end of a container which is disposed in a casing 142 and whose flange 148, which is stable in respect of shape, projects out of casing 142. As shown in FIG. 14, casing 142 has a peripherally extending groove 158, preferably in the region of the flange part projecting into casing 142. Snap noses 156 of the container when fitted into the connecting portion 154 engage into groove 158, whereby the container is releasably and positively lockingly connected to connecting portion 154.

Figure 16A:
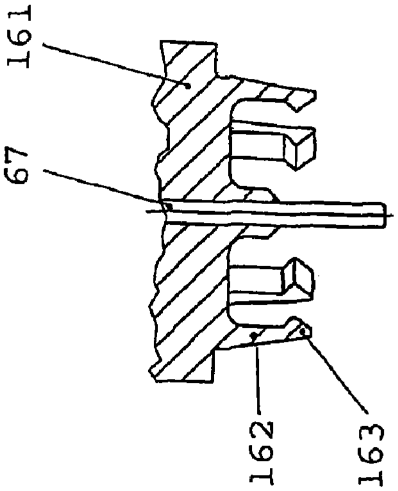
FIG. 16*a* is a sectional view of a second embodiment of a connecting portion of a container of the present invention.
Figure 16B:
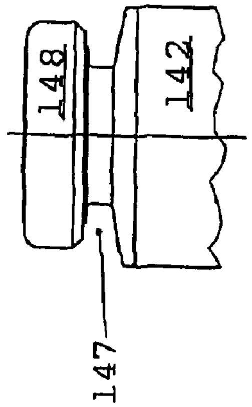
FIG. 16*b* is a side view of one end of the container of FIG. 16*a*.

FIGS. 16*a* and 16*b* show a further embodiment of a releasable, positively locking, push-in snap connection.

FIG. 16*a* is a view in cross-section through a connecting portion 161 which is disposed in the discharge device and which on its axis includes discharge connection member 67. Discharge connection member 67 is surrounded by a plurality of tongue-shaped snap hooks 162 with snap noses 163 whose flanks are beveled in both directions of movement of the container. Snap hooks 162 are disposed at an azimuthal spacing from each other.

FIG. 16*b* is a side view of the end of a container which is disposed in a casing 142 and whose flange 148, which is stable in respect of shape, projects out of casing 142. When the container is fitted into connecting portion 154, snap noses 163 engage into peripherally extending groove 147 of the part, which projects out of the casing, of the flange 148, whereby the container is releasably connected to the connecting portion in positively locking relationship.

The container according to the invention is particularly suitable as an interchangeable cartridge for inhalable medicament solutions in propellant-free atomizers. The filling volume of the container can be from 0.5 ml to 5 ml, preferably from 1 ml to 4 ml and particularly preferably from 1 ml to 3 ml or from 2 ml to 4 ml. Those solutions are discharged in a portion-wise manner with a respective dosage of 10 μl to 50 μl, preferably from 15 μl to 20 μl.

The casing diameter can be from 10 mm to 30 mm, preferably from 12 mm to 17 mm. The length of the container including the part, which projects out of the casing, of the flange which is stable in respect of shape can be from 20 mm to 60 mm, preferably from 30 mm to 50 mm.

The container according to the invention serves as a primary packaging means for accommodating a medicinal liquid which for example contains a medicament dissolved in a solvent. Suitable solvents are for example water, ethanol or mixtures thereof. The medicaments used are for example BEROTEC (fenoterol-hydrobromide; 1-(3,5-dihydroxyphenyl)-2-[[1-(4-hydroxybenzyl)-ethyl]-amino]-ethanol-hydrobromide), ATROVENT (ipratropium bromide), BERODUAL (combination of fenoterol-hydrobromide and ipratropium-bromide), SALBUTAMOL (or ALBUTEROL), COMBIVENT, OXIVENT (oxitropium bromide), BA 679 (tiotropium bromide), BEA 2108 (di-(2-thienyl)-glycol acid tropenol ester), FLUNISOLID, BUDESONID, BECLOMETHASON and others.

WO-98/27959 describes stabilized aqueous medicament preparations for the production of propellant-free aerosols for inhalation, the disclosure of which is incorporated herein by reference in its entirety. In particular, reference is directed to the formulations claimed therein and set forth in the examples.

Suitable medicament preparations in ethanol solution are set forth for example in WO-97/01329, the disclosure of which is incorporated herein by reference in its entirety. In particular, reference is directed to the active substances specified therein (see therein pages 2 and 3) and the stabilized formulations claimed therein.

What is claimed is:

1. A container for a medicament for use as an interchangeable cartridge in an inhaler, the container being gas-tight and liquid-tight, comprising:

- a sealed-edge foil bag which is collapsible at a differential pressure below 300 hPa (300 mbar), wherein said foil bag plastically and irreversibly collapses in a predetermined manner such that said foil bag retains its initial length after emptying, said foil bag having at least one welded seam of a substantially T-shaped or substantially V-shaped configuration to seal edges of said foil bag and close a first end of said foil bag;
- a one-piece flange sealingly connected to a second end of said foil bag for closing said second end of said foil bag, said flange having a guide passage formed therein for sealingly fitting said container onto a discharge connection member of the inhaler;
- a pierceable membrane to seal said container whereby said pierceable membrane is pierced by the discharge connection member when said container is fitted onto the discharge connection member,
- wherein said flange is a monolithic structure including said pierceable membrane and said guide passage, and
- said guide passage has an end portion that extends into an interior chamber of said foil bag, wherein said pierceable membrane is disposed at an end of or within said end portion.

2. The container according to claim 1, wherein said foil bag is made from a composite material comprising at least two layers.

3. The container according to claim 2, wherein a first layer of said composite material includes a metal selected from the group consisting of aluminum, gold, and copper.

4. The container according to claim 2, wherein said composite material comprises an inner foil of a plastic material and an outer foil of a metal material.

5. The container according to claim 2, wherein said composite material comprises two foils of different plastic materials.

6. The container according to claim 2, wherein said composite material comprises:

an inner foil made of a first plastic material, a diffusion-tight central layer; and an outer foil of a second plastic material, wherein the melting temperature of said second plastic material is higher than the melting temperature of said inner foil.

7. The container according to claim 6, wherein said diffusion-tight central layer is made from a material selected from the group consisting of a plastic material, a metal material, a glass and a ceramic.

8. The container according to claim 6, wherein said outer foil is made of polyethylene terephthalate.

9. The container according to claim 6, wherein said inner foil is made of a polyethylene copolymer of ethylene-acrylic acid.

10. The container according to claim 1, wherein said flange comprises a press fit within said guide passage for sealingly fitting the discharge connection member in said guide passage.

11. The container according to claim 10, wherein the press fit is a portion of said guide passage and comprises a smooth inside wall of an inside diameter of said guide passage which only slightly differs from an outside diameter of the discharge connection member.

12. The container according to claim 10, further comprising a plurality of bulge portions on an inside wall of said guide passage.

13. The container according to claim 12, wherein said plurality of bulge portions are of an elongate configuration and extend symmetrically in the axial direction of said guide passage.

14. The container according to claim 12, wherein said plurality of bulge portions form a plurality of ring portions on the inside wall of said guide passage.

15. The container according to claim 12, wherein said plurality of bulge portions are of a helical configuration.

16. The container according to claim 1, wherein the at least one welded seam of said foil bag has a substantially T -shaped configuration.

17. A container for a medicament for use as an interchangeable cartridge in an inhaler, the container being gas-tight and liquid-tight, comprising:

a sealed-edge foil bag which is collapsible at a differential pressure below 300 hPa (300 mbar), wherein said foil bag plastically and irreversibly collapses in a predetermined manner such that said foil bag retains its initial length after emptying, said foil bag including at least one welded seam of a substantially T-shaped or substantially V-shaped configuration to seal edges of said foil bag and close a first end of said foil bag;

a one-piece flange sealingly connected to a second end of said foil bag for closing said second end of said foil bag, said flange being fish-like in form and having a guide passage formed therein, wherein a portion of said guide passage has a press fit for sealingly fitting said container onto a discharge connection member of the inhaler; and a pierceable membrane to seal said container whereby said pierceable membrane is pierced by the discharge connection member when said container is fitted onto the discharge connection member, wherein said pierceable membrane is arranged between said press fit of said guide passage and an interior chamber of said foil bag.

18. A propellant gas-free atomizer with a discharge connection member for dispensing medicament in inhalable metered doses, comprising:

a container including:

a sealed-edge foil bag which is collapsible at a differential pressure below 300 hPa (300 mbar), wherein said foil bag plastically and irreversibly collapses in a predetermined manner such that said foil bag retains its initial length after emptying, said foil bag having at least one welded seam to seal edges of said foil bag and close a first end of said foil bag, a flange sealingly connected to a second end of said foil bag for closing said second end of said foil bag, said flange having a guide passage formed therein for sealingly fitting said container onto the discharge connection member, and a pierceable membrane to seal said container whereby said pierceable membrane is pierced by the discharge connection member when said container is fitted onto the discharge connection member, wherein said flange is a monolithic structure including said pierceable membrane and said guide passage is disposed at an end of or within said guide passage wherein said guide passage has an end portion that extends into said interior chamber of said foil bag, wherein said pierceable membrane is disposed at an end of or within said end portion; and an inhalable medicament preparation disposed in the container.

19. The atomizer according to claim 18, wherein the medicament is taken in a dosage of 1 μl to 50 μl.

20. The atomizer according to claim 18, wherein the medicament is taken in a dosage of 15 μl to 20 μl.

21. The atomizer according to claim 18, wherein the medicament is in a solution of ethanol, water, or a mixture thereof.

22. The atomizer according to claim 20, wherein the medicament includes at least one active substance selected from the group consisting of (fenoterol-hydrobromide; 1-(3,5-dihydroxyphenyl)-2-[[1-(4-hydroxybenzyl)-ethyl]-amino]-ethanol-hydrobromide), (ipratropium bromide), (combination of fenoterol-hydrobromide and ipratropium-bromide), (oxitropium bromide), (tiotropium bromide), (di-(2-thienyl)-glycol acid tropenol ester), and combinations thereof.

23. The container according to claim 18, wherein said guide passage has an end portion that extends into an interior chamber of said foil bag, wherein said pierceable membrane is disposed at an end of or within said end portion guide passage.

24. The container according to claim 18, wherein the at least one welded seam of said foil bag has a substantially T-shaped or substantially V-shaped configuration.

25. The container according to claim 18, wherein a portion of said guide passage has a press fit for fitting said container onto the discharge connection member, wherein said pierceable membrane is arranged between said press fit of said guide passage and an interior chamber of said foil bag.

26. A container for a medicament for use as an interchangeable cartridge in an inhaler, the container being gas-tight and liquid-tight, comprising:

a foil bag which is collapsible at a differential pressure below 300 hPa (300 mbar), wherein said foiled bag includes at least one welded seam to sealingly close a first end of said foil bag, wherein at least a portion of said welded seam extends partially in the longitudinal direction of said foil bag, wherein said foil bag plastically and irreversibly collapses in a predetermined manner and retains its initial length after emptying;

a one-piece flange sealingly connected to a second end of said foil bag for closing said second end of said foil bag, said flange having a guide passage formed therein, wherein said guide passage has a seal portion for sealingly fitting said container onto a discharge connection member of the inhaler, and wherein said guide passage has an end portion that extends into an interior chamber of said foil bag; and a pierceable membrane to seal said container whereby said pierceable membrane is pierced by the discharge connection member when said container is fitted onto the discharge connection member, wherein said pierceable membrane is disposed at an end of or within said end portion of said guide passage that extends into said interior chamber of said foil bag.

27. The container according to claim 26, wherein said pierceable membrane is arranged between said seal portion of said guide passage and said interior chamber of said foil bag.

28. The container according to claim 27, wherein said seal portion comprises at least one of a sealing location and a press fit.

29. The container according to claim 26, wherein the at least one welded seam of said foil bag has a substantially U-shaped configuration, a substantially T -shaped configuration, or a substantially V -shaped configuration.

30. The container according to claim 26, wherein said foil bag is a tubular foil without a longitudinal seam extending from the first end to the second end of the said foil bag.

31. The container according to claim 26, wherein said foil bag is a sealed-edge foil bag having a longitudinal seam extending from the welded seam to the second end of the said foil bag.

* * * * *